(12) United States Patent
Steinhardt et al.

(10) Patent No.: US 8,562,614 B2
(45) Date of Patent: Oct. 22, 2013

(54) DISPOSABLE CARTILAGE CUTTER

(75) Inventors: Uwe Steinhardt, Hirrlingen (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 433 days.

(21) Appl. No.: 12/774,351

(22) Filed: May 5, 2010

(65) Prior Publication Data
US 2010/0286693 A1 Nov. 11, 2010

(30) Foreign Application Priority Data

May 6, 2009 (DE) .................... 20 2009 006 583 U

(51) Int. Cl.
*A61B 17/00* (2006.01)
(52) U.S. Cl.
USPC ............................ 606/86 R; 606/79; 606/167
(58) Field of Classification Search
USPC ......... 606/79, 82–84, 86 R, 87–88, 167, 172, 606/184; 269/298 R, 302.1, 900; 30/123; 83/687, 691
See application file for complete search history.

(56) References Cited

U.S. PATENT DOCUMENTS

| | | | | |
|---|---|---|---|---|
| 5,060,387 A * | 10/1991 | Doucette | ........................ | 30/330 |
| 5,071,427 A * | 12/1991 | Stahl | ............................ | 606/172 |
| 5,364,401 A * | 11/1994 | Ferrante et al. | ................. | 606/84 |
| 6,513,803 B2 * | 2/2003 | Morales et al. | ............... | 269/290 |
| 7,216,574 B2 * | 5/2007 | Woods | ............................. | 83/397 |
| 8,230,769 B2 * | 7/2012 | Eisenkolb | ....................... | 83/607 |
| 2003/0125811 A1 * | 7/2003 | Bonutti | ....................... | 623/23.51 |
| 2006/0087067 A1 * | 4/2006 | Shamoon | ................. | 269/289 R |
| 2007/0262507 A1 * | 11/2007 | Bayer et al. | .................... | 269/305 |

FOREIGN PATENT DOCUMENTS

| | | | |
|---|---|---|---|
| EP | 0483567 | * | 10/1991 |
| EP | 0 483 567 | | 5/1992 |
| EP | 0483567 A1 | * | 5/1992 |

* cited by examiner

*Primary Examiner* — Todd Manahan
*Assistant Examiner* — Marcela I Shirsat
(74) *Attorney, Agent, or Firm* — Michael J. Striker

(57) ABSTRACT

A medical device that is composed of a sterilizable material, is used to create thin cartilage discs, and includes a device body and a cover with a plurality of holding devices, each of which includes a section that with a recess located in the top side of the device body, the recess being entirely or partially enclosed by a delimiting ridge, and being closable via a projection located on the top side of the cover, and in which the lateral delimiting ridge has a guide slot, into which a cutting blade is inserted and guided via an end face of the section and extends, at a distance that differs for each section, parallel to the bottom surface of the particular recess. It is therefore possible to create thin cartilage discs having certain, different thicknesses and a consistent level of quality, even without using the known shims.

20 Claims, 3 Drawing Sheets

DISPOSABLE CARTILAGE CUTTER

CROSS-REFERENCE TO RELATED APPLICATION

The invention described and claimed hereinbelow is also described in German Patent Application DE 20 2009 006 583.9 filed on Jun. 5, 2009. This German Patent Application, whose subject matter is incorporated here by reference, provides the basis for a claim of priority of invention under 35 U.S.C. 119(a)-(d).

BACKGROUND OF THE INVENTION

The present invention relates generally to a disposable cartilage cutter.

More particularly, the present invention relates to a medical cutting device that includes a device body and a cover, and is used to create thin cartilage discs, in the case of which a first holding device is provided that includes a first section that includes a first recess which is located in the top side of the device body, the first recess being entirely or partially enclosed by a first delimiting ridge, and being closable via a first projection which is located on the top side of the cover, and in which the first lateral delimiting ridge includes a first guide slot which is guided via an end face of the first section and extends, at a predetermined first distance, parallel to the bottom surface of the first recess.

A device of this type is known from EP 0 483 567 B1.

Time and time again, it becomes necessary for various medical purposes to cut thin, endogeneous cartilage discs out of a larger piece of cartilage, e.g., from the auricle, the tragus, the cartilaginous portion of the upper bony rib, or the nasal septum. For example, it may be necessary to examine special properties of the main body in greater detail, in particular under a microscope. In otorhinolaryngology, thin cartilage discs of this type are also required in many surgical applications, such as in the middle ear region to cover a middle ear prosthesis, to restore the posterior wall of the auditory meatus, or for the plastic repair of a defect of the tympanic membrane. Thin cartilage discs of this type are also used in many nasal surgeries, in order to perform functional or aesthetic corrections of the nose.

A cutting device of the type in question is described in EP 0 483 567 B1, using which thin cartilage discs having a thickness that is specifiable, within certain limits, may be cut out of a larger piece of cartilage quickly, reliably, and with a consistent level of quality. However, to obtain different thicknesses of the cartilage discs that are obtained, special shims having a known thickness must be placed in the cutting device. These shims, like the cutting device itself, must be thoroughly cleaned and kept sterile, and they must be handled in this manner separately before every operation, which is a time-consuming process that is susceptible to error. Considering that an average ENT hospital has three to four surgical suites, and that, at peak times, fifteen to twenty patients may be operated on in one day, it is possible that a cartilage cutter must be made available up to fifteen times a day. This poses a great logistical challenge in terms of supplying sterilized materials.

Moreover, handling the shims is not entirely easy. For example, due to their small size, it is not always possible to label them adequately and in an easily recognized manner, even though this is necessary in order to ensure that precisely the proper shim having the particular size that is required is available during the operation. In addition, special skills are required to insert the relatively small shims into the cutting device correctly, and to fix them in position therein.

SUMMARY OF THE INVENTION

In contrast, the object of the present invention is to improve a generic medical device of the type described initially, using the simplest technical means possible, in a simple and cost-favorable manner by ensuring that thin cartilage discs having certain different thicknesses may be created in a consistent level of quality, even without using the known shims.

According to the present invention, this object is attained in a manner that is surprisingly simple and effective in that at least one second holding device is provided that includes a second section that includes a second recess which is located in the top side of the device body, the second recess being entirely or partially enclosed by a second delimiting ridge, and being closable via a second projection which is located on the top side of the cover, and in which the second lateral delimiting ridge includes a second guide slot, into which a cutting blade is inserted, and which is guided via an end face of the second section and extends, at a predetermined second distance, parallel to the bottom surface of the second recess.

Since different distances between the particular guide slot and the corresponding bottom surface of the particular recess may be selected for different holding devices, the cutting device according to the present invention makes it possible to create cartilage discs having certain different thicknesses by using the different holding devices, without needing to use the known shims.

Furthermore, it has been shown that handling the new cutting device between the thumb and index finger gives the operating surgeon greater confidence when performing the actual cutting procedure. Due to their geometry and design, all of the parts may be moved toward each other safely and in a controlled manner.

A particularly simple and compact design of the cutting device according to the present invention is characterized by the fact that a third holding device is provided that includes a third section that includes a third recess which is located in the top side of the device body, the third recess being entirely or partially enclosed by a third delimiting ridge, and being closable via a third projection which is located on the top side of the cover, and in which the third delimiting ridge includes a third guide slot which is guided from an end face of the third section and extends, at a specified third distance, parallel to the bottom surface of the third recess, and which is used for the insertion of a cutting blade, and by the fact that the three holding devices are preferably situated relative to one another in the shape of a cross.

Experience has shown, in fact, that it is sufficient in most cases to provide three different thicknesses of the cartilage disc to be created for a middle ear operation, in order to create an optimal match for the particular circumstances of the patient. If a finer differentiation should be carried out nevertheless, it is also possible to use a plurality of these embodiments next to one another, in which case every individual cutting device should cover a different thickness range, and a precise selection may be made on the basis of the three different thicknesses in the selected thickness range that are offered.

A class of embodiments of the cutting device according to the present invention is very particularly preferred in which the cutting device is composed of a sterilizable plastic. As a result, the cutting device may be manufactured in a much more cost-favorable manner than the typical devices, which are composed of metal. The cutting device is delivered to the operating site in a sterile package, and the cutting device may be easily discarded after use. In addition, a sterile-packaged, disposable product of this type has the advantage that it is not necessary to perform time-consuming cleaning and sterilization of the cutting device before every operation, and the risk of infection is minimized, in contrast to the case in which sterilized materials are supplied, in which the risk of infection cannot be ruled out.

In developments of this class of embodiments, the cutting device is preferably manufactured using an injection-moulding procedure.

Embodiments of the present invention are also preferable in which the cover is attached to the device body via a material bridge, and is preferably foldable by 180°. It them becomes easily possible to screw the two parts of the holding devices together, as is known per se from EP 0 483 567 B1, in order to securely fix the piece of cartilage in position, out of which the desired cartilage disc should be cut.

In developments of these embodiments that are particularly easy to handle, the material bridge includes a predetermined bending line or narrowed region, about which the cover may be folded relative to the device body.

A variant of the above-described embodiments that is very particularly preferred is characterized by the fact that the injection point for the injection-moulding procedure is located on the predetermined bending line.

A further preferred class of embodiments of the cutting device according to the present invention is characterized by the fact that markings are formed on the sections of the device body and/or on the corresponding sections of the cover, on which the projections are formed; the markings indicate the particular predetermined distance from the guide slot to the bottom surface of the corresponding recess and, therefore, the thickness of the cartilage disc that may be obtained using the particular holding device.

In developments of these embodiments, the markings may include numbers that indicate the particular predetermined distance from the guide slot to the corresponding recess, and therefore, the thickness of the cartilage disc that is obtainable using the particular holding device, in the metric system of measurement, in particular in millimeters, or in the imperial system of measurement, in particular in inches.

As an alternative, the markings may also include graphical depictions, in particular scale marks, points, and the like, which indicate the particular predetermined distance from the guide slot to the bottom surface of the corresponding recess, and, therefore, the thickness that may be attained using the particular holding device of the cartilage disc to be created.

Variants of the above-described embodiments are ergonomically particularly favorable in which the markings are formed on the underside of the device body, opposite the recesses, and/or on the underside of the cover, opposite the projections.

In a further ergonomically favorable embodiment of the cutting device according to the present invention, convex and/or concave gripping aids are formed on the underside of the device body, opposite the recesses, and/or on the underside of the cover, opposite the projections, which are used for orientation purposes to apply pressure to the particular center of the projections.

In embodiments of the present invention, an enclosing border that extends along the edge may be provided on the underside of the cover, opposite the projections.

Likewise, in further embodiments, an enclosing wall may be provided on the top side of the device body, between the recesses, which encloses a working space that may be used for the pretreatment of a cartilage piece before cutting out the desired disc, or for the further processing of the cartilage disc that was cut out.

Round and/or oval templates that have different diameters may also be used to process the cartilage discs that are cut out; in embodiments of the cutting device according to the present invention, the templates are incorporated in a surface of the cutting device, in particular on the top side of the device body, in which the recesses are formed, preferably in the working space, and/or on the top side of the cover, on which the projections are formed.

Embodiments of the cutting device according to the present invention are very particularly advantageous in which a measurement scale is formed in a surface of the cutting device, in particular on the top side of the device body, in which the recesses are formed, preferably in the working space, and/or on the top side of the cover, on which the projections are formed, using which the cartilage pieces to be processed, and/or the cartilage discs that were cut out may be easily measured.

In embodiments of the present invention, the bottom surfaces of the recesses and/or the surfaces of the projections may be roughened in order to better hold the cartilage pieces to be processed.

One class of embodiments is characterized by the fact that the lateral delimiting segments, in which the guide slots are formed, are each formed as single pieces that enclose the recesses.

In an alternative class of embodiments, the lateral delimiting ridges, in which the guide slots are formed, are each formed as a plurality of individual ridges, as is known per se from EP 0 483 567 B1.

Embodiments of the cutting device according to the present invention that prove effective in practical applications are those in which the cutting blade is a knife blade composed of metal, in particular a razor blade, and in which the cutting blade is retained in a knife holder that is preferably composed of plastic.

In simple embodiments of these embodiments, the knife holder may be designed as a single piece and include a slot for insertion of the cutting blade.

In alternative developments, the knife holder is designed as two pieces and is foldable, in order to hold the cutting blade, thereby making it easier to replace the cutting blade.

Other developments of the above-described embodiments are characterized by the fact that the knife holder includes at least one surface, in which round and/or oval templates, which preferably have different diameters, are formed.

Preferably, a border that encloses the knife holder and extends along the edge is provided, which increases the plane-area moment and, therefore, the stability of the holder.

Finally, another development is characterized by the fact that the knife holder includes at least one and preferably a plurality of through-openings.

Further features and advantages of the present invention result from the detailed description of embodiments of the invention presented below with reference to the figures in the drawing which shows the details that are essential to the present invention. Further features and advantages of the present invention also result from the claims. The individual features may be realized individually, or they may be combined in any possible manner in different variants of the present invention.

Embodiments of the present invention are depicted in the schematic drawing and are described in greater detail in the description that follows.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
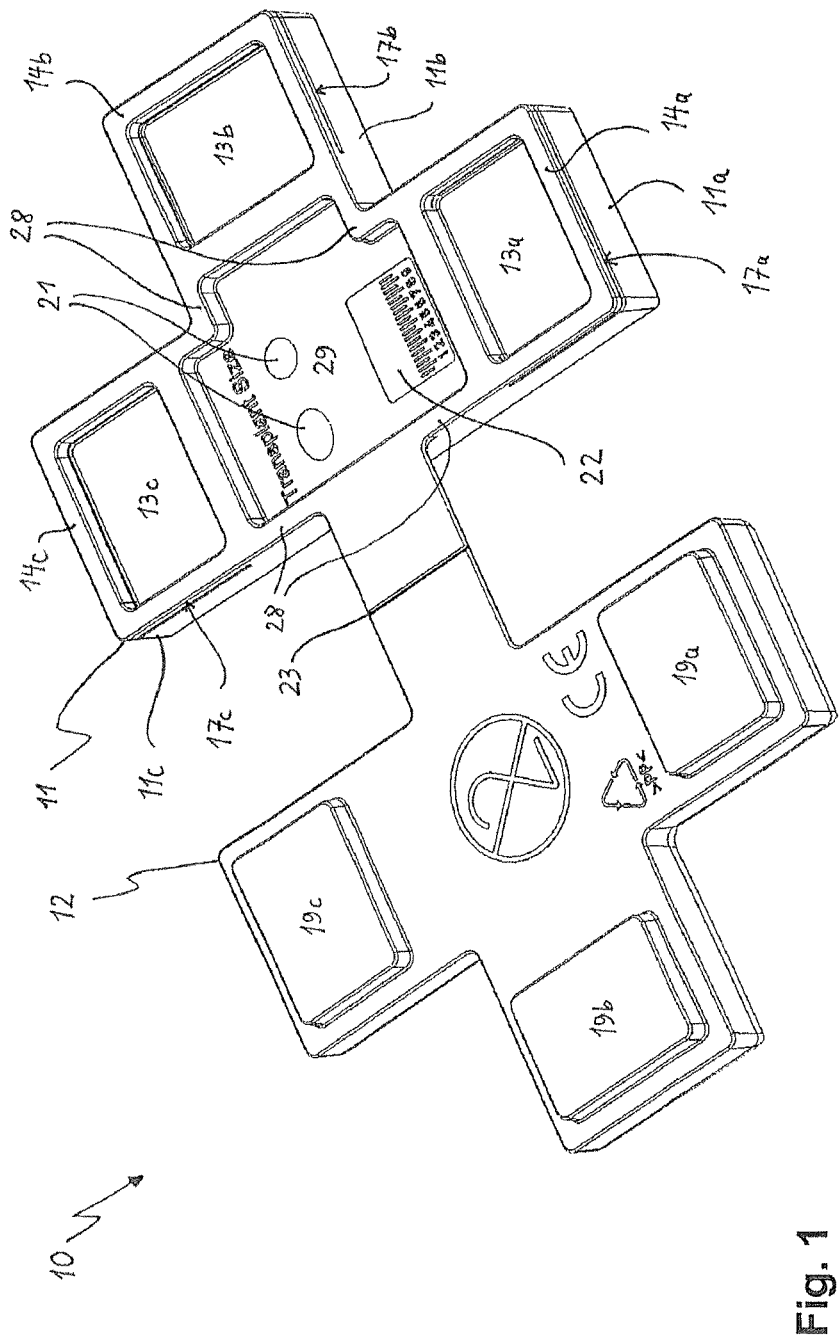
FIG. 1 shows a schematic, spacial depiction of the top side of an embodiment of the cutting device according to the present invention that includes three holding devices situated in the shape of a cross.
Figure 2:
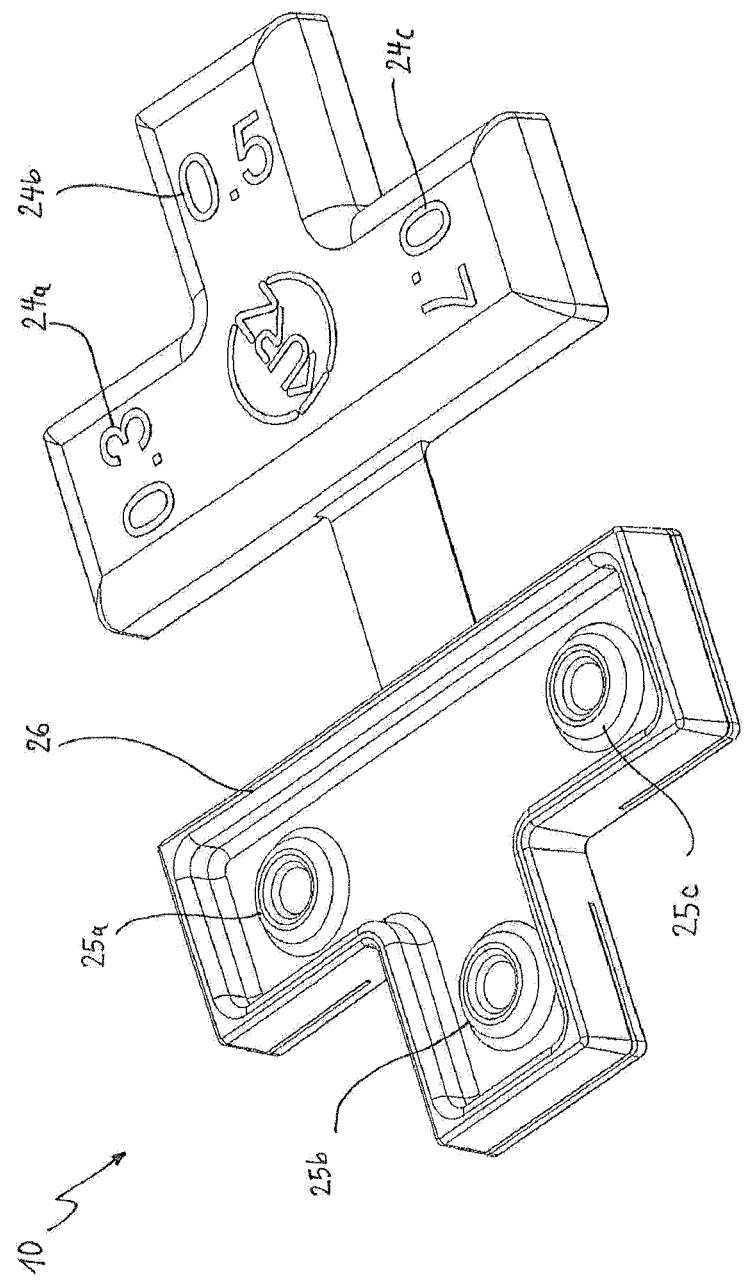
FIG. 2 shows a view of the underside of the embodiment depicted in FIG. 1.

The embodiment of medical cutting device 10, according to the present invention, which is depicted in a schematic, spacial manner in the figures of the drawing, is used to create a thin cartilage disc from a larger piece of cartilage, and is made of a sterilizable material, preferably a sterilizable plastic, via an injection-moulding procedure in particular. It includes a device body 11 and a cover 12.

In addition to a first holding device, which is used to hold the cartilage piece while a cartilage disc is cut, at least one second holding device is provided according to the present invention, and, in the present embodiment, a third holding device is also provided. In the embodiment that is shown, the three holding devices are located relatively close to one another, in the shape of a cross, for ergonomic reasons.

Each of the holding devices includes a section 11a, 11b, 11c that includes a recess 13a, 13b, 13c which is located in the top side of device body 11 and is enclosed by a single-pieced delimiting ridge 14a, 14b, 14c in entirety—or, in embodiments that are not depicted in the drawing, only partially, if so chosen, by a plurality of individual ridges in each case—and which is closable by a projection 19a, 19b, 19c that is located on the top side of cover 12. Lateral delimiting ridge 14a, 14b, 14c includes a guide slot 17a, 17b, 17c, into which a cutting blade 18 is inserted, and which is guided via an end face of section 11a, 11b, 11c, and extends, at predetermined distance that differs for each holding device, parallel to the bottom surface of recess 13a, 13b, 13c. Bottom surfaces of recesses 13a, 13b, 13c and/or the surfaces of projections 19a, 19b, 19c are preferably roughened in order to better hold the cartilage pieces to be processed.

In the embodiment of the present invention that is shown, cover 12 is attached to device body 11 via a material bridge having a predetermined bending line 23, and is foldable by 180° relative to device body 11. The injection point for manufacturing the cutting device according to the present invention using an injection-moulding procedure may be located on predetermined bending line 23.

Furthermore, the embodiment shown in the drawing is characterized by the fact that markings 24a, 24b, 24c are formed, as numbers, on sections 11a, 11b, 11c of device body 11 and indicate the particular predetermined distance, in millimeters in the present embodiment, from guide slot 17a, 17b, 17c to the bottom surface of corresponding recess 13a, 13b, 13c, and, therefore, the thickness of the cartilage disc that may be obtained using the particular holding device. As an alternative, the markings may also indicate the numerical values of the thickness in the imperial system of measurement, in particular in inches. As an alternative or in addition thereto, the markings may also include graphical depictions, in particular scale marks, points, or the like.

Markings 24a, 24b, 24c are typically formed on the underside of device body 11, opposite recesses 13a, 13b, 13c, and/or on the underside of cover 12, opposite projections 19a, 19b, 19c.

In addition, covex and/or concave gripping aids 25a, 25b, 25c and, preferably, an enclosing border 26 that extends along the edge are provided on the underside of cover 12, opposite projections 19a, 19b, 19c, or, in alternative embodiments of the present invention, on the underside of device body 11 opposite recesses 13a, 13b, 13c. An enclosing wall 28 that encloses a working space 29 is provided on the top side of device body 11, between recesses 13a, 13b, 13c.

Round and oval templates 21, which have different diameters and are used to further process the cartilage discs that were created, and a measurement scale 22 for measuring the cartilage discs that were processed are formed in a surface of cutting device 10—that is, in the embodiment shown, in working space 29 on the top side of device body 11, in which recesses 13a, 13b, 13c are formed.

Figure 3:
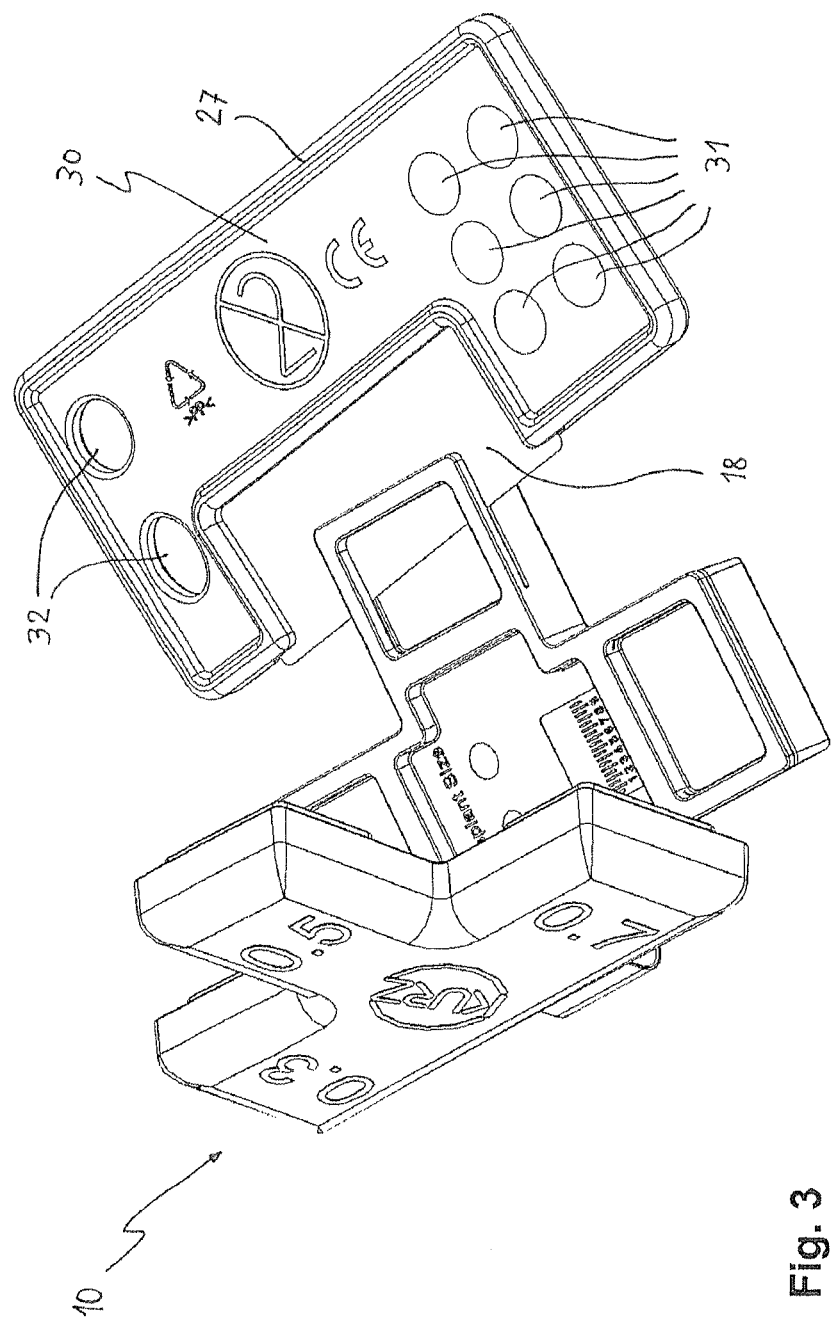
FIG. 3 shows a view of the embodiment of FIG. 1, in which the cover is folded about a predetermined bending line, and in which a cutting blade, including a knife holder, has been slid into the guide slot of one of the holding devices.

Cutting blade 18 is typically a knife blade that is composed of metal, in particular a razor blade. In the embodiment shown in FIG. 3, cutting blade 18 is held in a single-pieced knife holder 30 that is preferably composed of plastic and includes a slot for insertion of cutting blade 18. In embodiments of the cutting device according to the present invention, which are not shown in the drawing, knife holder 30 may also have a different design, e.g., a two-pieced design, and may be designed to be foldable in order to hold cutting blade 18.

In the embodiment that is shown, knife holder 30 includes at least one surface, in which round and/or oval templates 31 having different diameters are formed. In addition, a border 27 that encloses knife holder 30 and extends along the edge is provided that encloses a further working space, and knife holder 30 includes through-holes 32 that may be round and/or oval, for example.

It will be understood that each of the elements described above, or two or more together, may also find a useful application in other types of constructions differing from the types described above.

While the invention has been illustrated and described as embodied in a disposable cartilage cutter, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. A medical cutting device for creating a thin cartilage disc, comprising:
a device body having a first holding device including a first section with a first recess in a top side of said device body and at least partially enclosed by a first lateral delimiting ridge;
a cover having a first projection located on a top side of said cover and closing said first recess, wherein said first lateral delimiting ridge includes a first guide slot which is guided via an end face of said first section and extends at a predetermined first distance parallel to a bottom surface of said first recess;

a cutting blade inserted in said first guide slot of said first lateral delimiting ridge; wherein the cutting device is composed of a sterilizable material, and wherein said device body has at least one second holding device having a second section which includes a second recess located in the top side of said device body and at least partially enclosed by a second delimiting ridge, wherein said cover has a second projection which is located on the top side of said cover and closes said second recess, and wherein said second lateral delimiting ridge includes a second guide slot which is guided via an end face of said second section and extends at a predetermined second distance parallel to a bottom surface of said second recess, wherein said predetermined second distance is different than said predetermined first distance, and wherein a cutting blade is inserted into said second guide slot; and markings formed on sections selected from the group consisting of said sections of said device body, said sections of said cover on which said projections are formed, and both, said markings indicating a particular predetermined distance from said guide slot to said bottom surface from a corresponding one of said guide slots to said bottom surface of a corresponding line of said recesses and therefore a thickness of a cartilage disc that may be obtained using a corresponding one of said holding devices; and elements selected from the group consisting of round templates and oval templates having different diameters and formed in a surface of the cutting device, in an area selected from the group consisting of said top side of said device body in which said recesses are formed in a working space, on said top side of said cover on which said projections are formed, and both, said templates being configured to further process said thin cartilage disc.

2. The cutting device as defined in claim 1, wherein said device body has a third holding device having a third section which includes a third recess located in the top side of said device body and at least partially enclosed by a third delimiting ridge, while said cover has a third projection located on the top side of said cover and closing said third recess, and wherein said third delimiting ridge includes a third guide slot which is guided via an end face of said third section and extends at a predetermined third distance parallel to a bottom surface of the third recess.

3. The cutting device as defined in claim 1, wherein said cutting device is composed of a sterilizable plastic and formed as an injection-molded device with an injection point for an injection-molding process located on a predetermined bending line.

4. The cutting device as defined in claim 1, wherein said cover is attached to said device body via a material bridge and is foldable by 180°; and wherein said material bridge includes a predetermined structure selected from the group consisting of a bending line and a narrowed region, about which said cover is foldable relative to said device body.

5. The cutting device as defined in claim 1, wherein each of said device body and said cover has an underside, and further comprising gripping aids selected from the group consisting of convex gripping aids and concave gripping aids, and formed in an area selected from the group consisting of on the underside of said device body opposite said recesses, on the underside of said cover opposite said projections, and both.

6. The cutting device as defined in claim 1, wherein said cover has an underside, and further comprising an enclosing border that extends along an edge provided on the underside of said cover opposite said projections.

7. The cutting device as defined in claim 1, further comprising an enclosing wall provided on the top side of said device body between the recesses.

8. The cutting device as defined in claim 1, further comprising a measurement scale formed in a surface of the cutting device in an area selected from the group consisting of said top side of said device body in which said recesses are formed in the working space, on said top side of said cover on which said projections are formed, and both, said measurement scale being configured to measure said thin cartilage disc.

9. The cutting device as defined in claim 1, wherein elements selected from the group consisting of bottom surfaces of said recesses, surfaces of said projections, and both are roughened.

10. The cutting device as defined in claim 1, wherein said lateral delimiting segments are each formed as single pieces that encloses said recesses.

11. The cutting device as defined in claim 10, wherein each of said lateral delimiting segments comprises a plurality of individual segments.

12. The cutting device as defined in claim 1, wherein said cutting blade is a knife blade composed of metal and held in a knife holder composed of plastic.

13. The cutting device as defined in claim 12, wherein said knife holder is a single piece holder and includes a slot for insertion of said cutting blade.

14. The cutting device as defined in claim 12, wherein said knife holder has two pieces and is foldable to hold said cutting blade.

15. The cutting device as defined in claim 12, further comprising a border that encloses said knife holder and extends along an edge of said knife holder.

16. The cutting device as defined in claim 12, wherein said knife holder includes at least one through-opening.

17. A medical cutting device for creating a thin cartilage disc, comprising:

a device body having, a first holding device including a first section with a first recess in a top side of said device body and at least partially enclosed by a first lateral delimiting ridge;

a cover having a first projection located on a top side of said cover and closing said first recess, wherein said first lateral delimiting ridge includes a first guide slot which is guided via an end face of said first section and extends at a predetermined first distance parallel to a bottom surface of said first recess;

a cutting blade inserted in said first guide slot of said first lateral delimiting ridge; wherein the cutting device is composed of a sterilizable material and wherein said device body has at least one second holding device having a second section which includes a second recess located in the top side of said device body and at least partially enclosed by a second delimiting ridge, wherein said cover has a second projection which is located on the top side of said cover and closes said second recess, and wherein said second lateral delimiting ridge includes a second guide slot which is guided via an end face of said second section and extends at a predetermined second distance parallel to a bottom surface of said second recess, wherein said predetermined second distance is different than said predetermined first distance, and wherein a cutting blade is inserted into said second guide slot; and markings formed on sections selected from the group consisting of said sections of said device body, said sections of said cover on which said projections are formed, and both, said markings indicating a particular predetermined distance from said guide slot to said bottom surface from a corresponding one of said guide slots to said bottom surface of a corresponding line of said recesses and therefore a thickness of a cartilage disc that may be obtained using a corresponding one of said holding devices, wherein said cutting blade is a knife blade composed of metal and held in a knife holder composed of plastic, and wherein said knife holder includes at least one surface in which templates selected from the group consisting of round templates and oval templates and having different diameters are formed said templates being configured to further process said thin cartilage disc.

18. A medical cutting device for creating a thin cartilage disc, comprising:

a device body having a first holding device including a first section with a first recess in a top side of said device body and at least partially enclosed by a first lateral delimiting ridge;

a cover having a first projection located on a top side of said cover and closing said first recess, wherein said first lateral delimiting ridge includes a first guide slot which is guided via an end face of said first section and extends at a predetermined first distance parallel to a bottom surface of said first recess;

a cutting blade inserted in said first guide slot of said first lateral delimiting ridge; wherein the cutting device is composed of a sterilizable material, and wherein said device body has at least one second holding device having a second section which includes a second recess located in the top side of said device body and at least partially enclosed by a second delimiting ridge, wherein said cover has a second projection which is located on the top side of said cover and closes said second recess, and wherein said second lateral delimiting ridge includes a second guide slot which is guided via an end face of said second section and extends at a predetermined second distance parallel to a bottom surface of said second recess, wherein said predetermined second distance is different than said predetermined first distance, and wherein a cutting blade is inserted into said second guide slot; and markings formed on sections selected from the group consisting of said sections of said device body, said sections of said cover on which said projections are formed, and both, said markings indicating a particular predetermined distance from said guide slot to said bottom surface from a corresponding one of said guide slots to said bottom surface of a corresponding line of said recesses and therefore a thickness of a cartilage disc that may be obtained using a corresponding one of said holding devices, wherein each of said device body and said cover has an underside, wherein said markings are formed in an area selected from the group consisting of on the underside of said device body opposite said recesses, on the underside of said cover opposite said projections, and on both.

19. A medical cutting device for creating a thin cartilage disc, comprising:

a device body having a first holding device including a first section with a first recess in a top side of said device body and at least partially enclosed by a first lateral delimiting ridge;

a cover having a first projection located on a top side of said cover and closing said first recess, wherein said first lateral delimiting ridge includes a first guide slot which is guided via an end face of said first section and extends at a predetermined first distance parallel to a bottom surface of said first recess;

a cutting blade inserted in said first guide slot of said first lateral delimiting ridge wherein the cutting device is composed of a sterilizable material, and wherein said device body has at least one second holding device having a second section which includes a second recess located in the top side of said device body and at least partially enclosed by a second delimiting ridge, wherein said cover has a second projection which is located on the top side of said cover and closes said second recess, and wherein said second lateral delimiting ridge includes a second guide slot which is guided via an end face of said second section and extends at a predetermined second distance parallel to a bottom surface of said second recess, wherein said predetermined second distance is different than said predetermined first distance, and wherein a cutting blade is inserted into said second guide slot; and elements selected from the group consisting of round templates and oval templates having different diameters and formed in a surface of the cutting device, in an area selected from the group consisting of said top side of said device body in which said recesses are formed in a working space, on said top side of said cover on which said projections are formed, and both, said templates being configured to further process said thin cartilage disc.

20. A medical cutting device for creating a thin cartilage disc, comprising:

a device body having a first holding device including a first section with a first recess in a top side of said device body and at least partially enclosed by a first lateral delimiting ridge;

a cover having a first projection located on a top side of said cover and closing said first recess, wherein said first lateral delimiting ridge includes a first guide slot which is guided via an end face of said first section and extends at a predetermined first distance parallel to a bottom surface of said first recess;

a cutting blade inserted in said first guide slot of said first lateral delimiting ridge; wherein the cutting device is composed of a sterilizable material, and wherein said device body has at least one second holding device having a second section which includes a second recess located in the top side of said device body and at least partially enclosed by a second delimiting ridge, wherein said cover has a second projection which is located on the top side of said cover and closes said second recess, and wherein said second lateral delimiting ridge includes a second guide slot which is guided via an end face of said second section and extends at a predetermined second distance parallel to a bottom surface of said second recess, wherein said predetermined second distance is different than said predetermined first distance, and wherein a cutting blade is inserted into said second guide slot, wherein said cutting blade is a knife blade composed of metal and held in a knife holder composed of plastic, and wherein said knife holder includes at least one surface in which templates selected from the group consisting of round templates and oval templates and having different diameters are formed said templates being configured to further process said thin cartilage disc.

\* \* \* \* \*